United States Patent [19]

Ichikawa et al.

[11] 4,082,804

[45] Apr. 4, 1978

[54] PROCESS FOR PREPARING 2-AMINO-1-BUTANOL BY REACTION OF THE TARTARATE WITH AN ALKALINE EARTH METAL COMPOUND

[75] Inventors: Yataro Ichikawa, Fuchu; Toru Sawaki, Iwakuni; Yuitsu Honda, Kawasaki, all of Japan

[73] Assignee: Teijin Limited, Minamihonmachi, Japan

[21] Appl. No.: 736,683

[22] Filed: Oct. 28, 1976

[51] Int. Cl.$^2$ .................... C07C 89/04; C07C 91/04
[52] U.S. Cl. ................ 260/584 R; 260/707; 260/DIG. 35
[58] Field of Search .... 260/584 R, DIG. 8, DIG. 35, 260/707

[56] References Cited

U.S. PATENT DOCUMENTS 3,553,257  1/1971  Halmos et al. ............ 260/584 R X

OTHER PUBLICATIONS

Radke et al., "JACS", vol. 76, pp. 2801–2803 (1954).

*Primary Examiner*—Daniel E. Wyman
*Assistant Examiner*—John J. Doll
*Attorney, Agent, or Firm*—Sughrue, Rothwell, Mion, Zinn and Macpeak

[57]  ABSTRACT

A process for preparing 2-amino-1-butanol by reacting L-tartarate of 2-amino-1-butanol with an aqueous slurry alkaline earth metal compound in such a way that some L-tartarate of 2-amino-1-butanol remains in the reaction system throughout the entire time of reaction to produce a precipitate of L-tartarate of the alkaline earth metal which comprises crystals which are sufficiently large so that they have excellent filterability and give a high yield of 2-amino-1-butanol. Highly purified 2-amino-1-butanol can be obtained by subjecting the thus obtained filtrate to rectification.

18 Claims, 3 Drawing Figures

FIG. 1 (100X)
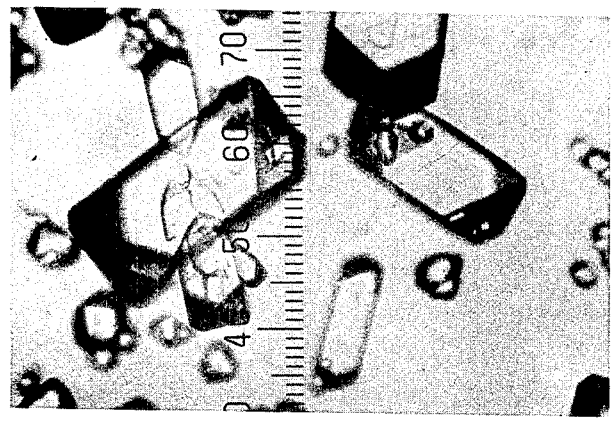
FIG. 2 (100X)
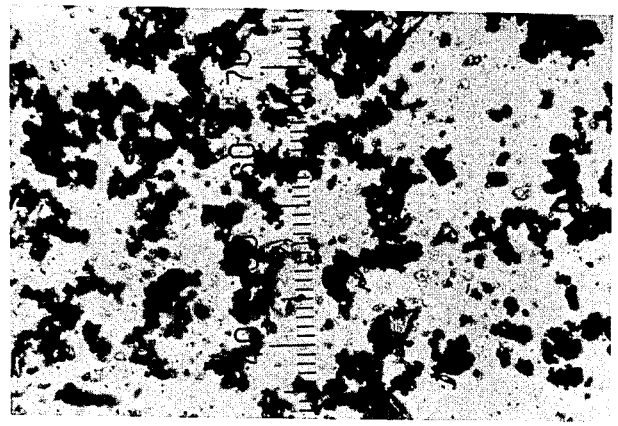
FIG. 3 (100X)
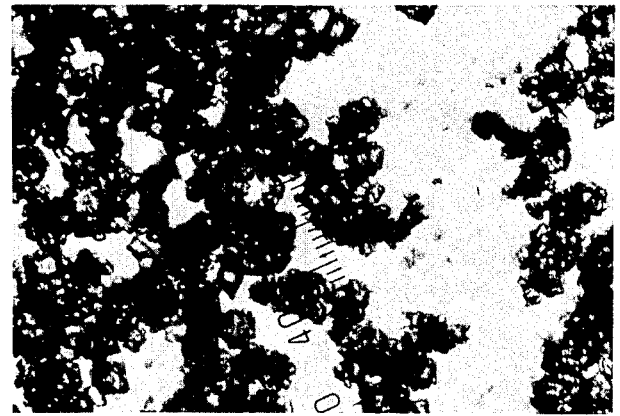

PROCESS FOR PREPARING 2-AMINO-1-BUTANOL BY REACTION OF THE TARTARATE WITH AN ALKALINE EARTH METAL COMPOUND

BACKGROUND OF THE INVENTION

1. Field of the Invention

This invention relates to a process for preparing 2-amino-1-butanol from the L-tartarate of 2-amino-1-butanol.

It is well known that 2-amino-1-butanol is industrially advantageous as an intermediate of ethanbutol[2,2'-ethylendiimino)-di-1-butanol] which is valuable for use in medicines, e.g., as disclosed in British Pat. No. 961,317.

Having an asymmetric carbon, 2-amino-1-butanol has two optical isomers, i.e., the dextro-form (d) and the levoform (l). Of the two ethanbutols synthesized from the aforesaid two optical isomers, however, only the ethanbutol synthesized from d-2-amino-1-butanol has a pharmacological effect, and the ethanbutol synthesized from l-2-amino-1-butanol not only is pharmacologically ineffectual, but also has undesirable side effects.

Therefore, it is necessary to separate d- from l-2-amino-1-butanol by optical resolution. The d-2-amino-1-butanol thus separated can be used as an intermediate of ethanbutol; on the other hand, the l-2-amino-1-butanol thus separated can be used as a starting material for optical resolution, after racemization.

2. Description of the Prior Art

As for the method of the optical resolution mentioned above, a well known method comprises reacting d- and l-2-amino-1-butanol with L-tartarate to form diastereoisomers, which are then optically resolved by recrystallization in an aqueous solvent, such as water or an aqueous solution of an organic solvent such as an alcohol in water solution, etc. Then the obtained crystal of L-tartarate of d-2-amino-1-butanol are reacted with an alkaline earth metal compound in an aqueous solvent to precipitate an L-tartarate of the alkaline earth metal compound. Free d-2-amino-1-butanol is recovered in the solvent.

According to our research, however, in the reaction of the L-tartarate of d-2-amino-1-butanol or l-2-amino-1-butanol with an alkaline earth metal compound in an aqueous solvent, e.g., water, when the aforesaid two components are mixed in the conventional way, e.g., by random charging, the obtained crystals of the L-tartarate of the alkaline earth metal compound have small diameters and poor filterability. In addition, the filter cake obtained has a high water content and moreover presents difficulties in rinsing. Therefore, one is unable to maintain the yield of d-2-amino-1-butanol or l-2-amino-1-butanol at high levels with ease. It is desirable to form the precipitates which don't contain a large amount of small crystals having dimensions less than $15\mu \times 15\mu$.

By the present invention, however, and taking the method of mixing into special consideration, gross crystals of the L-tartarate of the alkaline earth metal compound can be obtained and d- or l-2-amino-1-butanol can be obtained in high yields with ease.

SUMMARY OF THE INVENTION

A first object of this invention is to provide a process for preparing a crystalline solid of the L-tartarate of alkaline earth metal compound in which the crystals have large diameters and excellent filterability.

A second object of this invention is to provide a filtration process for preparing a filter cake which has a low water content and can be rinsed easily during the filtration.

A third object of this invention is to provide a process for recovering d-2-amino-1-butanol or l-2-amino-1-butanol in good yield.

These and other objects of the invention will become apparent from the following specification.

According to this invention, the above objects and advantages are achieved by reacting the L-tartarate of 2-amino-1-butanol with an alkaline earth metal compound under conditions which ensure the presence of the L-tartarate of 2-amino-1-butanol in the reaction system from beginning to end, to form a precipitate of the L-tartarate of the alkaline earth metal compound which has excellent filterability and also to form a filter cake which has a low water content and which can be rinsed easily. In this manner the yield of 2-amino-1-butanol is maintained at a high level.

BRIEF DESCRIPTION OF THE DRAWING

To illustrate the objects and advantages of this invention photomicrographs (100 × magnification) of the filter cakes which were obtained by different processes are provided as follows:

FIG. 1 is a photograph of the crystals of calcium tartarate obtained according to Example 1;

FIG. 2 is a photograph of the crystals of calcium tartarate obtained according to Comparison Example 1; and FIG. 3 is a photograph of the crystals of calcium tartarate obtained according to Comparison Example 2.

DETAILED DESCRIPTION OF THE INVENTION

This invention relates to a process for preparing 2-amino-1-butanol easily and in high yield by carrying out the reaction of the L-tartarate of 2-amino-1-butanol with an alkaline earth metal compound to extricate the 2-amino-1-butanol from the L-tartarate thereof so that gross, readily separable crystals of the resulting L-tartarate of the alkaline earth metal are obtained.

This invention is not specifically limited by the purity of the L-tartarate of 2-amino-1-butanol in terms of d-, l-forms, or by the method of preparing L-tartarate of 2-amino-1-butanol which is used as a starting material. For instance, L-tartarate of 2-amino-1-butanol prepared by the process described in U.S. Pat. No. 3,553,257 or British Pat. No. 1,198,923 or J.A.C.S. 76 2,801 (1954) is useful in the present invention.

Alkaline earth metal compounds which can be used in the present invention include, for example:

i. the carbonates of alkaline earth metals, such as calcium carbonate, barium carbonate and strontium carbonate;

ii. the oxides of alkaline earth metals, such as calcium oxide, barium oxide and strontium oxide; and iii. the hydroxides of alkaline earth metals, such as calcium hydroxide, barium hydroxide and strontium hydroxide.

Of the above examples, calcium carbonate, calcium oxide and calcium hydroxide are preferable.

The reaction in this invention is preferably conducted in a solvent such as water, or an aqueous solution of an organic solvent, especially in water.

The significant point of this invention is that at least some L-tartarate of 2-amino-1-butanol is present in the system during the entire time that the reaction is being conducted. In the reaction of the L-tartarate of 2-amino-1-butanol with an added alkaline earth metal compound, the reaction rate is sufficiently high to form 2-amino-1-butanol and the L-tartarate of the alkaline earth metal compound in a short time. Therefore, an amount of alkaline earth metal compound and an equivalent amount of L-tartarate of 2-amino-1-butanol are consumed quickly upon addition to the L-tartarate of 2-amino-1-butanol.

As referred to in the preceding paragraph, the significant point is that the L-tartarate of 2-amino-1-butanol continues to exist all the while in the above reaction system.

In spite of fixing the conditions which enable one to maintain the aforesaid state of reaction system, crystals as shown in FIG. 3 may be formed when a large amount of alkaline earth metal compound is added in a short time, and this is an undesirable result.

Therefore, in the present invention, it is especially advantageous that the L-tartarate of 2-amino-1-butanol is reacted with the alkaline earth metal compound so slowly that the formation of fine particles of the L-tartarate of the alkaline earth metal is prevented.

Preferred embodiments of this invention include, for example, i. a process in which an alkaline earth metal compound is added little-by-little into a reaction system in which the L-tartarate of 2-amino-1-butanol has already been charged;

ii. a process in which the L-tartarate of 2-amino-1-butanol and an almost equivalent, but lesser, amount of alkaline earth metal compound are added together into a reaction system little-by-little; and iii. a process in which a small amount of the L-tartarate of 2-amino-1-butanol is first charged, and then the L-tartarate of 2-amino-1-butanol and an equivalent amount of alkaline earth metal compound are added together little-by-little.

In the above examples, processes (i) and (iii) are preferable and the process (i) is especially advantageous.

In the present invention, the crystallization of the L-tartarate of the alkaline earth metal, which is formed by reacting the L-tartarate of 2-amino-1-butanol with the alkaline earth metal compound, is carried out at a temperature in the range of about 30° to 80° C, especially 35° to 65° C.

In this invention the solution of the L-tartarate of 2-amino-1-butanol should preferably be used at a concentration in the range of from about 4 to 70% by weight.

When the solution of the L-tartarate of 2-amino-1-butanol is used at a concentration lower than about 4% by weight, the concentration of 2-amino-1-butanol extricated by the reaction becomes low and, therefore, disadvantageously it requires the use of a great amount of effort and energy to recover 2-amino-1-butanol by condensating the filtrate.

On the other hand, when the solution of the L-tartarate of 2-amino-1-butanol is used at a concentration higher than about 70% by weight, the density of the slurry of the L-tartarate of the alkaline earth metal becomes high and it is disadvantageous to handle a slurry of such high density.

In this invention, the slurry of the alkaline earth metal compound should preferably be used at a density of from about 1 to 50% by weight. When the slurry of the alkaline earth metal compound is used at a density lower than about 1% by weight, the concentration of 2-amino-1-butanol extricated by the reaction becomes low, and it is disadvantageous to recover 2-amino-1-butanol from such a dilute solution by condensing the filtrate.

On the other hand, when the density is higher than about 50% by weight, it is disadvantageous to handle the dense slurries of the alkaline earth metal compound and of the L-tartarate of the alkaline earth metal.

Gross crystals of the L-tartarate of the alkaline earth metal having dimensions larger than about $40\mu$ thick $\times$ $50\mu$ long are, therefore, advantageously formed according to the present invention.

In this invention, the equivalent ratio of alkaline earth metal compound to L-tartarate of 2-amino-1-butanol can be selected from a comparatively extensive range. The point is that some of the L-tartarate of 2-amino-1-butanol is always present during the formation of the crystals of the L-tartarate of the alkaline earth metal by the reaction of the alkaline earth metal compound with the L-tartarate of 2-amino-1-butanol. Furthermore, an excess of the alkaline earth metal compound may be present to a certain degree under circumstances wherein the crystals of the L-tartarate of the alkaline earth metal are not formed to any substantial extent.

Consequently, the equivalent ratio of the total amount of the alkaline earth metal compound fed to the total amount of the L-tartarate of 2-amino-1-butanol fed at the terminal stage of the reaction is between 0.5 and 2.0 and preferably is between 0.7 and 1.4. Furthermore, it is preferable to maintain the above ratio at slightly more than 1.0 in order to obtain a high yield of 2-amino-1-butanol.

In this invention, the mixing of the L-tartarate of 2-amino-1-butanol with the alkaline earth metal compound is carried out, not randomly, but little-by-little, carefully, to satisfy the above condition. The feed rate, especially, is determined by procedures such as aforementioned embodiments (i), (ii) and (iii), the volume of reactor, orientation and numbers of inlet, kind of alkaline earth metal compound, and so on.

The point is that alkaline earth metal compound should not be fed at a rate greatly in excess of the consumption rate of alkaline earth metal compound during the reaction with the L-tartarate of 2-amino-1-butanol.

For instance, in the case of the above-described embodiment (i), suitable gross crystals were obtained by titrating at the rate of about 0.15 - less than 1.0, preferably 0.2 – 0.6 mol [Ca(OH)$_2$] per mol [L-tartarate of 2-amino-1-butanol] per hour in the 300 ml reactor at 50° C with agitation.

The slurry formed by the reaction and crystallization is filtered by centrifugal separation or filtration, and the filtrate thus obtained is charged into a distillation column. A highly purified 2-amino-1-butanol can be obtained by rectification of this material.

The following examples are given to illustrate the invention in greater detail. Unless otherwise indicated, all parts, percentages, ratios and the like are by weight and all procedures were conducted at room temperature and atmospheric pressure.

EXAMPLE 1

36 parts of acidic L-tartarate of d-2-amino-1-butanol, which was obtained through 3-round crystallization using methanol as a solvent, was dissolved in 73.1 parts of water. Thereafter, the above solution was titrated for 1.5 hrs., with a mixture of 13.4 parts of calcium hydroxide and 53.6 parts of water while the temperature was kept at 50° C with stirring.

The obtained crystals of calcium tartarate were crystals having an appearance like grains of rice and dimensions in the range of $50 - 100\mu \times 50 - 100\mu$ as shown in FIG. 1.

The slurry was filtered by forced filtration under reduced pressure with the use of aspirators. The filtration was carried out easily, and the water content of the cake thus filtered was 20% on a wet basis. The amine was recovered in a yield of 99%.

COMPARISON EXAMPLE 1

44.6 parts of water was mixed with 11.1 parts of calcium hydroxide and the mixture was titrated for 1.5 hrs, with a solution of 36 parts of acidic L-tartarate of d-2-amino-1-butanol (the same as was used in Example 1) in 44.6 parts of water while being kept at 50° C with stirring.

The obtained crystals of calcium tartarate were fine amorphous particles having dimensions of $3 - 20\mu \times 3 - 20\mu$ as shown in FIG. 2.

The slurry was filtered by forced filtration under a reduced pressure with the use of aspirators. The filtration was not carried out easily, and the water content of the cake thus obtained was 35% on a wet basis. The amine was recovered in a yield of 90%.

COMPARISON EXAMPLE 2

36 parts of acidic L-tartarate of d-2-amino-1-butanol (the same as was used in Example 1) was dissolved in 73.1 parts of water. Then, 13.4 parts of calcium hydroxide was added at once while being kept at 50° C with stirring and agitation was continued for an hour at 50° C. The crystals formed were fine amorphous particles having dimensions of $4 - 18\mu \times 4 - 18\mu$ as shown in FIG. 3. The resulting slurry was filtered by forced filtration under a reduced pressure using aspirators.

The filtration was not carried out easily, and the water content of the cake obtained was 33% on a wet basis. The amine was recovered in a yield of 85%.

EXAMPLE 2

An aqueous solution of 31.4 parts of acidic L-tartarate of d-2-amino-1-butanol (the same as was used in Example 1) in 31.4 parts of water and a mixture of 9.3 parts of calcium hydroxide and 37.2 parts of water was titrated continuously for 6 hours into the reactor, in which 30 parts of water had already been charged, and the temperature was kept at 50° C with good agitation.

After titration, the agitation was continued for 30 minutes at 50° C, and the formed slurry was filtered by forced filtration under a reduced pressure.

The crystals of calcium tartarate obtained were columnar, having dimensions of $30 - 40\mu \times 90 - 120\mu$, and the water content of the cake was 25.1% on a wet basis. The amine was recovered in a yield of 93.3%.

EXAMPLE 3

3.0 parts of acidic L-tartarate of d-2-amino-1-butanol (the same as was used in Example 1) and 30 parts of water were charged in the reactor with agitation at 50° C.

Then, a solution of 29.9 parts of acidic L-tartarate of d-2-amino-1-butanol, the same one as used in Example 1, in 29.9 parts of water and the mixture of 9.3 parts of calcium hydroxide and 37.2 parts of water were titrated continuously for 6 hours thereinto.

After titration, the agitation was continued for 30 minutes at 50° C to form columnar crystals of calcium tartarate.

The crystals had dimensions of $33 - 41\mu \times 85 - 110\mu$.

The obtained slurry was filtered under reduced pressure and the water content of the filter cake was 26.7% on a wet basis. The amine was recovered in a yield of 89.1%.

What is claimed is:

1. In a method for the production of 2-amino-1-butanol by the reaction of the L-tartarate of 2-amino-1-butanol with an alkaline earth metal compound to produce a crystalline precipitate of the L-tartarate of the alkaline earth metal and a filtrate containing recoverable 2-amino-1-butanol, the improvement comprising:

gradually adding an aqueous slurry of the alkaline earth metal compound to said L-tartarate of 2-amino-1-butanol so as always to maintain said L-tartarate of 2-amino-1-butanol present in excess in the reaction system during the reaction, the rate of addition of said alkaline earth metal compound into contact with said L-tartarate of 2-amino-1-butanol being from about 0.15 to less than 1.0 mol of said alkaline earth metal compound per mol of said L-tartarate of 2-amino-1-butanol per hour, to precipitate crystals of the L-tartarate of said alkaline earth metal having dimensions of at least about $40\mu$ thick $\times$ $50\mu$ long.

2. The process of claim 1 in which the reaction is carried out at a temperature of 30° to 80° C.

3. The process of claim 1 in which the equivalent ratio of used alkaline earth metal compound to used L-tartarate of 2-amino-1-butanol is between 0.5 and 2.0.

4. The process of claim 1 in which the reaction is carried out in water.

5. The process of claim 1 in which calcium hydroxide, calcium oxide or calcium carbonate is the said alkaline earth metal compound.

6. The process of claim 3, wherein said equivalent ratio is more than 1.0

7. In a method for the production of 2-amino-1-butanol by the reaction of the L-tartarate of 2-amino-1-butanol with an alkaline earth metal compound to produce a crystalline precipitate of the L-tartarate of the alkaline earth metal and a filtrate containing recoverable 2-amino-1-butanol, the improvement comprising:

gradually and simultaneously adding the L-tartarate of 2-amino-1-butanol and almost equivalent but lesser, amount of an aqueous slurry of the alkaline earth metal compound into the reaction system, to precipitate crystals of the L-tartarate of said alkaline earth metal having dimensions of at least about $40\mu$ thick $\times$ $50\mu$ long.

8. The process of claim 7, in which the reaction is carried out at a temperature of 30° to 80° C.

9. The process of claim 7, in which the equivalent ratio of used alkaline earth metal compound to used L-tartarate of 2-amino-1-butanol is between 0.5 and 2.0.

10. The process of claim 7, in which the reaction is carried out in water.

11. The process of claim 7, in which calcium hydroxide, calcium oxide or calcium carbonate is the said alkaline earth metal compound.

12. The process of claim 9, wherein said equivalent ratio is more than 1.0.

13. In a method for the production of 2-amino-1-butanol by the reaction of the L-tartarate of 2-amino-1-butanol with an alkaline earth metal compound to produce a crystalline precipitate of the L-tartarate of the alkaline earth metal and a filtrate containing recoverable 2-amino-1-butanol, the improvement comprising:

charging a small amount of the L-tartarate of 2-amino-1-butanol and subsequently gradually and simultaneously adding the L-tartarate of the 2-amino-1-butanol and an equivalent amount of an aqueous slurry of the alkaline earth metal compound, to precipitate crystals of the L-tartarate of said alkaline earth metal having dimensions of at least 40μ thick × 50μ long.

14. The process of claim 13, in which the reaction is carried out at a temperature of 30° to 80° C.

15. The process of claim 13, in which the equivalent ratio of used alkaline earth metal compound to used L-tartarate of 2-amino-1-butanol is between 0.5 and 2.0.

16. The process of claim 13, in which the reaction is carried out in water.

17. The process of claim 13, in which calcium hydroxide, calcium oxide or calcium carbonate is the said alkaline earth metal compound.

18. The process of claim 15, wherein said equivalent ratio is more than 1.0.

* * * * *